(12) United States Patent
Brauers et al.

(10) Patent No.: US 9,044,170 B2
(45) Date of Patent: Jun. 2, 2015

(54) BALLISTOCARDIOGRAM ANALYSIS METHOD AND DEVICE

(75) Inventors: Andreas Brauers, Aachen (DE); Xavier Louis Marie Antoine Aubert, Brussels (BE)

(73) Assignee: Koninklijke Philips N.V., Eindhoven (NL)

( * ) Notice: Subject to any disclaimer, the term of this patent is extended or adjusted under 35 U.S.C. 154(b) by 1141 days.

(21) Appl. No.: 13/002,877

(22) PCT Filed: Jul. 6, 2009

(86) PCT No.: PCT/IB2009/052932
§ 371 (c)(1),
(2), (4) Date: Jan. 6, 2011

(87) PCT Pub. No.: WO2010/004502
PCT Pub. Date: Jan. 14, 2010

(65) Prior Publication Data
US 2011/0118614 A1    May 19, 2011

(30) Foreign Application Priority Data
Jul. 11, 2008   (EP) .................... 08160206

(51) Int. Cl.
| A61B 5/04 | (2006.01) |
| A61B 5/11 | (2006.01) |
| A61B 5/024 | (2006.01) |
| A61B 5/113 | (2006.01) |
| A61B 5/00 | (2006.01) |
| A61B 5/0452 | (2006.01) |

(52) U.S. Cl.
CPC ........... *A61B 5/1102* (2013.01); *A61B 5/04007* (2013.01); *A61B 5/411* (2013.01); *A61B 5/0452* (2013.01); *A61B 5/02438* (2013.01); *A61B 5/113* (2013.01); *A61B 5/7207* (2013.01)

(58) Field of Classification Search
USPC .................. 600/481, 483, 484, 500, 527, 534
See application file for complete search history.

(56) References Cited

U.S. PATENT DOCUMENTS

| 4,738,264 A | 4/1988 | Orlando |
| 2003/0233034 A1 | 12/2003 | Varri et al. |
| 2006/0079798 A1 | 4/2006 | Bischoff et al. |
| 2006/0122525 A1 | 6/2006 | Shusterman |

FOREIGN PATENT DOCUMENTS

| WO | 2006137067 A2 | 12/2006 |
| WO | 2008057883 A2 | 5/2008 |

OTHER PUBLICATIONS

Kuo et al: "On Certain Abnormal Ballistic Complexes: Their Relationships to Other Mechanical and Electrical Events of the Cardiac Cycle"; Circulation, vol. 1952, No. 6, pp. 74-81.

*Primary Examiner* — Carl H Layno
*Assistant Examiner* — Jon Eric C Morales

(57) ABSTRACT

The present invention discloses a method and signal processing device (620) for analyzing a ballistocardiogram (BCG). The actual energy content of the cardiac part of the BCG in a predefined time window is determined and compared with a reference value. A difference between the actual energy content and the reference energy content exceeding a predefined threshold is indicative of the presence of an arrhythmia in the evaluated part of the BCG because the force exerted by an arrhythmic ventricular contraction, if at all present, is typically substantially smaller than the force exerted by a ventricular contraction of a regular heartbeat. This insight facilitates a more accurate detection of the presence of arrhythmias in a BCG compared to BCG detection schemes based on a heart rate analysis.

12 Claims, 5 Drawing Sheets

BALLISTOCARDIOGRAM ANALYSIS METHOD AND DEVICE

TECHNICAL FIELD OF THE INVENTION

The present invention relates to a method of analyzing a ballistocardiogram.

The present invention relates to a signal processing device for analyzing a ballistocardiogram.

BACKGROUND TO THE INVENTION

Electrocardiographs (ECGs) play an important role in the detection of many different heart conditions. One of the problems associated with the diagnosis of a heart condition in a patient is that the symptoms indicating the existence of the heart condition may be infrequent, which makes it possible that the heart condition remains undiagnosed for a prolonged period of time, thus exposing the patient to an increased health risk which in extreme cases can lead to the death of the patient.

In order to improve the size of the ECG data set on which the medical practitioner may base his diagnosis, a patient is sometime fitted with a so-called Holter monitor for long-term monitoring of the heart function. A Holter monitor is essentially a portable ECG, which improves the chance that an event is monitored that is indicative of a certain heart condition. However, Holter monitors can cause discomfort to the wearer of the monitor, which is less than ideal from a patient care perspective.

An alternative method to accurately monitor the heart function of a patient was discovered in the 1950s. This method, which uses a so-called ballistocardiograph (BCG), has since gained attention in medical research. A BCG typically comprises one or more sensors mounted in a stationary object in contact with the patient's body, e.g. a bed or a chair that can detect the forces exerted by the patient's body caused by the recoil forces of the blood on the arteries when being pumped out of the (left) ventricle of the heart. This technique has found some useful applications such as in the context of home monitoring, e.g. of chronic patients. This is because a BCG is more convenient for the patient, since the patient no longer has to wear the sensors and/or recording device that are typically associated with a Holter monitor.

An example of such a BCG device is disclosed in U.S. Pat. No. 4,738,264. The device includes a ballistic sensor that may be placed in a bed, and is arranged to monitor the heart rate and the respiration rate of the person sleeping in the bed and to produce an alarm system if combined integrated energy of the combined heart rate and respiration signal during a predefined time window falls under a predefined threshold. This is for instance useful in the early detection of symptoms leading to sudden infant death syndrome (cot or crib death), which is typically preceded by a slowing down of the respiratory and/or heart rate.

However, this prior art device provides data of limited intermediate diagnostic relevance only, because only heart conditions that are characterized by the combination of a fluctuating heart rate and a fluctuating breathing pattern can be detected, e.g. syncope. In contrast, arrhythmias caused by heart conditions such as sick sinus syndrome in which ectopic heart beats may occur or one or more heart beats may be missed do not cause a change in the patient's breathing pattern. Since the breathing component of a BCG dominates the energy content of the BCG signal, it is difficult to detect such arrhythmias.

Moreover, the detection of arrhythmias such as caused by partial or complete AV block, in which the conduction channels, e.g. the AV channel, between the sino-atrial (sinus) node located in the right atrium of the heart and the ventricles are at least partially blocked. Typically, such arrhythmias do not cause a fluctuation in the heart rate such that they cannot be easily detected by the prior art device.

The present invention seeks to provide a method of analyzing a BCG signal that facilitates the detection of at least certain types of arrhythmias in the BCG signal. The present invention further seeks to provide a signal processing device for analyzing a BCG signal that facilitates the detection of at least certain types of arrhythmias in the BCG signal.

SUMMARY OF THE INVENTION

According to a first aspect of the present invention, there is provided a method of analyzing a ballistocardiogram, comprising selecting a time window of the ballistocardiogram, said time window comprising a cardiac component signal incorporating a plurality of heart beats; defining a reference energy content for said time window; calculating an actual energy content for the cardiac component signal in said time window; comparing the actual energy content with the reference energy content; and generating a further signal when a difference between the actual energy content and the reference energy content exceeds a predefined threshold.

The present invention is based on the realization that arrhythmias cause a distinct variation in the energy content of the cardiac component of the ballistocardiogram. Hence, by determining the actual energy content of the ballistocardiogram over a certain time period, e.g. by means of integration, and comparing the actual energy content with a predefined energy content indicative of the energy content of a proper periodic heart rate during said time period, a difference between the actual energy content and the predefined energy content is indicative of the occurrence of an arrhythmia in the monitored heart rhythm. Hence, when this difference exceeds a predefined threshold, a further signal may be generated that signals the likely presence of an arrhythmia in the evaluated time window.

It will be appreciated that the detection of an arrhythmia in itself is not a diagnosis of any medical condition. Arrhythmias may be caused by many different types of conditions, for which further testing usually is required before the patient can be correctly diagnosed. In fact, even a healthy heart can exhibit rare arrhythmias. Hence, the detection of an arrhythmia merely is an indication of the possible presence of a medical condition.

The predetermined energy content may be derived using a content value associated with a known good heart rate. Alternatively, the method further comprises determining a heart rate from said time window, and wherein the step of defining a reference energy content comprises calculating the energy content of a part of the cardiac component signal incorporating a single heart beat and multiplying the calculated energy content by the determined heart rate such that an on-the-fly determination of the reference energy content is obtained. This has the advantage that the actual energy content is correlated to the actual heart rate of the patient, which improves the accuracy of the detection of the arrhythmia if present.

In a preferred embodiment, the method further comprises defining a further time window of the ballistocardiogram by displacing the time window by a predefined amount of time. Such a sliding window approach has the advantage that the energy content of each window remains substantially constant as long as each window has captured a perfectly periodic heart beat. Hence, a deviation from this substantially constant energy content signals the presence of an arrhythmia.

In an embodiment, the actual energy content of the time window is used as the reference energy content for the further time window when the actual energy content of the time window is indicative of the absence of an arrhythmia therein. This facilitates an efficient implementation of the sliding window approach.

Advantageously, the method further comprises generating the cardiac component signal by separating the cardiac component signal from a respiratory component signal of the ballistocardiogram to facilitate a more accurate detection of an arrhythmia.

In a further preferred embodiment, the method further comprises determining a respiration pattern during said time window; and modulating the cardiac component signal in accordance with the determined respiration pattern. It has been found that the pressure on a BCG sensor is increased during inhalation and decreased during exhalation, which has a marked effect on the amplitude of the cardiac component signal during such events. Hence, by modulating the cardiac component signal in accordance with the determined respiration pattern, the respiratory influences on the amplitudes of the cardiac component signal, and therefore on its energy content, may be reduced or even filtered out.

For instance, said modulating may comprise increasing the amplitude of the signal during an inhalation process and reducing the amplitude of the signal during an exhalation process.

According to a further aspect of the present invention, there is provided a signal processing device for analyzing a ballistocardiogram, wherein the processing device is arranged to implement the various embodiments of the method of the present invention. Such a signal processing device facilitates the detection of arrhythmias in a ballistocardiogram, as discussed above.

The signal processing device of the present invention may be incorporated in a system further comprising at least one ballistic sensor coupled to the signal processing device. Such a system allows for the recording of the ballistocardiogram as well as for the detection of arrhythmias therein.

The ballistocardiograph sensor may be integrated in means for supporting body weight such as a cushion, a mattress or a piece of furniture such as a chair or a bed. The system may further comprise an output device such as a loudspeaker or a display device for providing an output signal in response to the further signal.

BRIEF DESCRIPTION OF THE DRAWINGS

Embodiments of the invention are described in more detail and by way of non-limiting examples with reference to the accompanying drawings, wherein.

Figure 1:
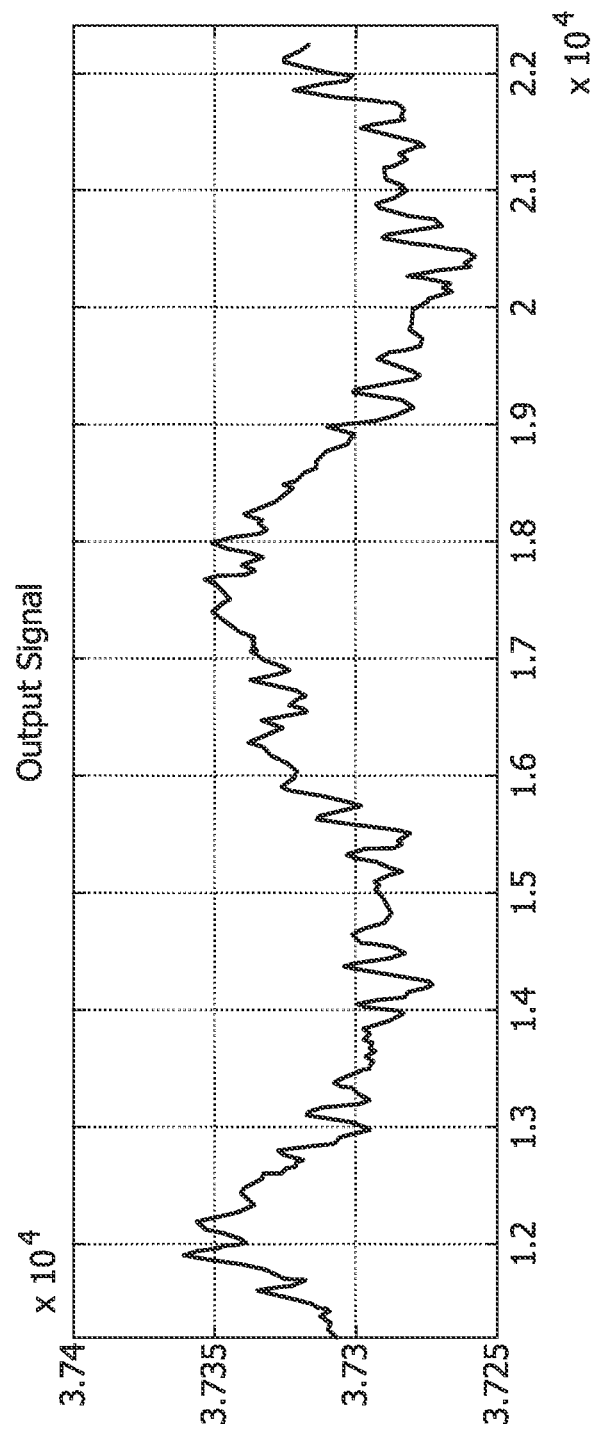
FIG. 1 depicts the raw data of a typical ballistocardiogram.

It should be understood that the Figures are merely schematic and are not drawn to scale. It should also be understood that the same reference numerals are used throughout the Figures to indicate the same or similar parts. In the detailed description of the drawings, the abbreviation BCG will be used to refer to a ballistocardiogram.

DETAILED DESCRIPTION OF THE EMBODIMENTS

FIG. 1 shows a typical BCG. The signal shown in FIG. 1 has been picked up using a single foil-like ballistic sensor placed below the thorax of a lying subject. The signal shown in FIG. 1 comprises a low frequency component generated by respiratory movements of the subject, as well as a periodic high frequency component related to the heart rate of the subject. In the context of the present invention, the phrase ballistic sensor is intended to include any sensor suitable for recording a BCG.

It will be clear to the skilled person that to obtain a BCG with a good signal to noise ratio, it is paramount that the subject should be stationary, e.g. resting, over the sensor. Larger movements, i.e. movements other than those caused by the subject's respiration and heart rate, would dominate the signal and thus make an evaluation difficult.

In case of the presence of signal perturbations caused by such larger movements in parts of the BCG, the BCG may be segmented in useful areas, i.e. areas in which the recorded signal is not perturbed by larger movements, and perturbed areas. The useful areas may be used for further analysis, as will be discussed in more detail later. The segmentation in useful areas and perturbed areas may be realized by evaluating the energy content of the respective areas, e.g. by means of signal integration. This will provide a good quality segmentation since the presence of a larger movement in a signal area significantly increases the amplitude of the BCG signal in that area, thus corresponding to a significantly larger energy content for the perturbed signal.

Figure 2A:
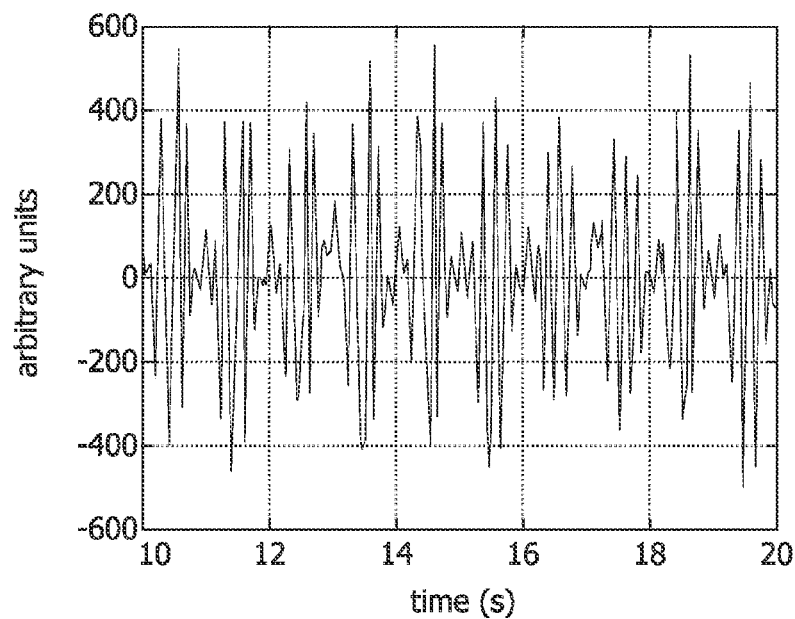
FIG. 2a depicts the cardiac component signal of the raw data.
Figure 2B:
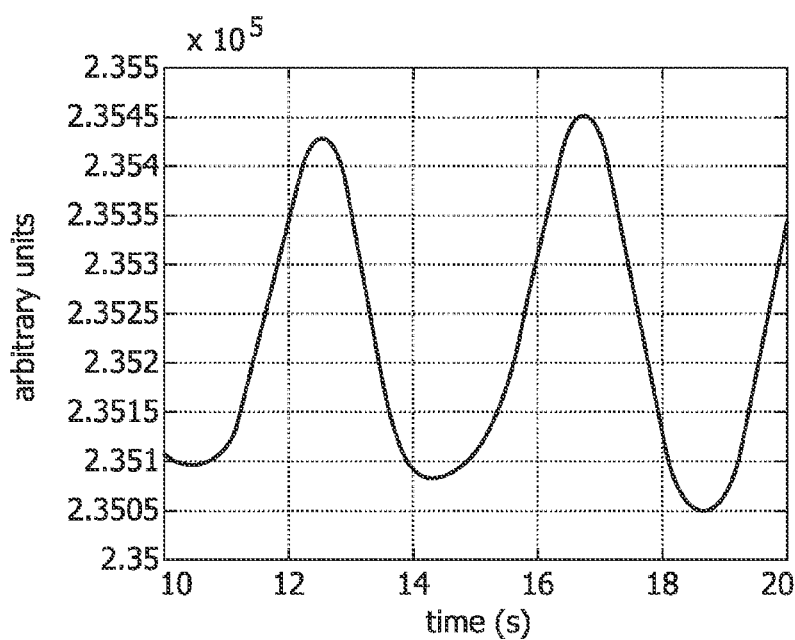
FIG. 2b depicts the respiratory component of the raw data.

The BCG may be separated into a cardiac component signal shown in FIG. 2a and a respiratory component signal shown in FIG. 2b. This separation may be realized in any suitable way, for instance by the use of appropriate band pass filters. Since a heart rate typically lies in a range of 45-180 Beats per Minute (BPM), a band pass filter may be used in the frequency range of 0.75-3.0 Hz, and may typically use a 1 Hz setting during a period of sleep of the subject, when the heart rate typically resides at the lower end of the given range.

The breathing cycle rate typically lies in the 3-30 Cycles per Minute (CPM) range. Consequently, a band pass filter in the 0.05-0.5 Hz range may be used, which may use a setting of around 0.25 Hz during a period of sleep of the subject, when the breathing rate typically resides at the lower end of the given range).

It can be seen that the respiratory pattern of FIG. 2b constitutes a relatively simple sinusoidal signal, which may be evaluated in the time domain, e.g. by locating maxima, minima, or zero crossings with suitable plausibility checks.

In contrast, the complex cardiac component signal in FIG. 2a reflects a series of complex movements of the heart. In addition, the exact footprint of the measured signal will depend on the transfer characteristics of the mechanical system of subject, carrier and sensor, e.g. patient, bed, foil, which may for example vary with the position of the subject.

As will be known to the skilled person, due to the complexity of the cardiac component signal, the determination of the subject's heart rate in a BCG is less straightforward than in an ECG. In a standard ECG, this heart rate may be derived by identifying the R-peaks in the ECG trace and measuring a number of R-R intervals, e.g. on a beat to beat basis, from which the average heart rate can be readily derived. However, the BCG is usually evaluated over a period of several heart beats either using a spectral method or using methods in the time domain that evaluate the reoccurrence of certain patterns, like e.g. an evaluation of the autocorrelation function of the BCG, e.g. the cardiac component thereof. Usually, prior to such an evaluation the BCG is filtered in order to remove undesired high and low frequency components from the signal.

The use of these techniques to determine the average heart rate from a BCG, e.g. the cardiac component signal thereof, the signal period, which will be also referred to as the signal time window, used for the heart rate estimation needs to cover more than one beat, so a beat to beat evaluation is difficult. A regular heart beat within this time window is required for an accurate estimation of the heart rate. The analysis of this signal may for instance be done using spectral methods or by trying to identify reoccurring patterns, e.g. using an auto correlation function. In both cases, several pulses (>2) have to be taken into account for an estimation of the heart rate which results in a blurring of the real beat to beat interval over several periods. The presence of certain arrhythmias in the BCG, like ectopic beats or missing beats either perturbs the estimation of the heart rate or may even go unnoticed.

It is recognized that the topic of cardiac (ventricle) arrhythmias is quite complex. Basically, the cardiac rhythm is controlled by specialized "pacemaker" cells located in the sino-atrial (SA) node, the firing rate of which being in turn ruled by the autonomous and central nervous systems. Broadly speaking, there are cardiac arrhythmias caused by irregular activation of the sinus-atrial node, like ectopic beats or extra-systole and there are arrhythmias caused by a bad or incomplete propagation of the electrical impulse arising from the sinus-atrial node, i.e. partial or complete heart block, where the impulse fails to reach the ventricles, causing the absence of a ventricular contraction. In the first case of ectopic beats, the electrical impulse does lead to a ventricular contraction, often of weaker amplitude, while in the second case an electrical activity may be seen in the ECG but without mechanical pumping counterpart.

This problem of accurate arrhythmia detection in a BCG has been addressed by the present invention by the determination of the actual energy content of the cardiac component signal of the BCG in a time window under evaluation. The present invention is particularly suited for detecting irregular ventricular contractions because such contractions have a distinctly different energy content in the cardiac component of a BCG compared to regular ventricular contractions. This will be demonstrated by two examples.

Figure 3:
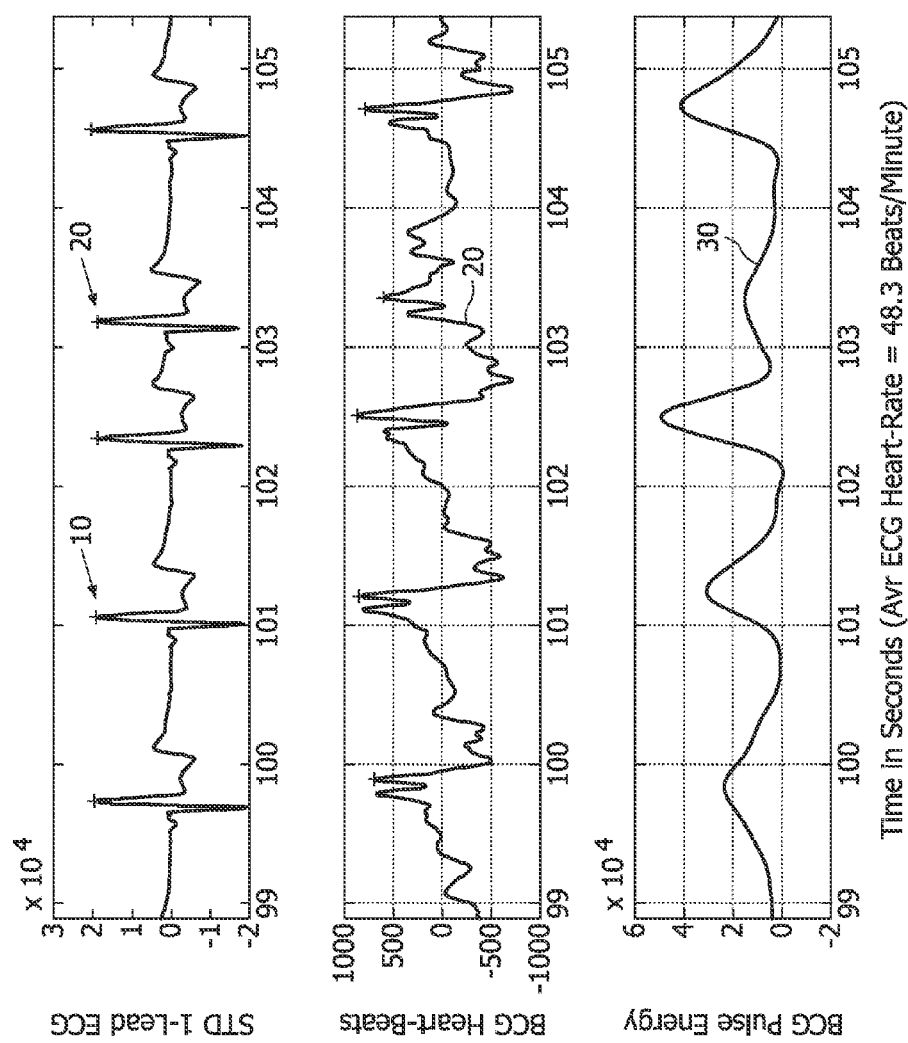
FIG. 3 depicts an atrial arrhythmia captured by a one-lead ECG, the cardiac component of a BCG as well as the energy contained in the cardiac component of the BCG.

FIG. 3 shows a time window of approximately 6.5 seconds in which the heart rate of a subject is monitored using a one-lead ECG (top pane), a BCG (middle pane, cardiac component shown) and in which the energy content of the cardiac component of the recorded BCG is determined in accordance with an embodiment of the method of the present invention (bottom pane). The R-peaks 10 in the ECG are marked with a '+'-sign. The resulting mechanical ventricular contractions causing the systolic ejection of blood from the heart that can be observed in the BCG are marked accordingly.

In FIG. 3, the arrhythmias can be observed as irregular RR intervals with an alternation of long (1,375 sec) and short (0.84 sec) beat-to-beat intervals that are visible in the ECG as well as in the BCG signal plots. The presence of a premature beat 20, i.e. an extra systole, has a distinct impact on the energy content 30 of the ventricular contraction observed in the cardiac component of the BCG corresponding to the extra systole. It can be seen in the bottom pane that the energy content 30 is much smaller than the energy content of the regular systolic heart beats.

Figure 4:
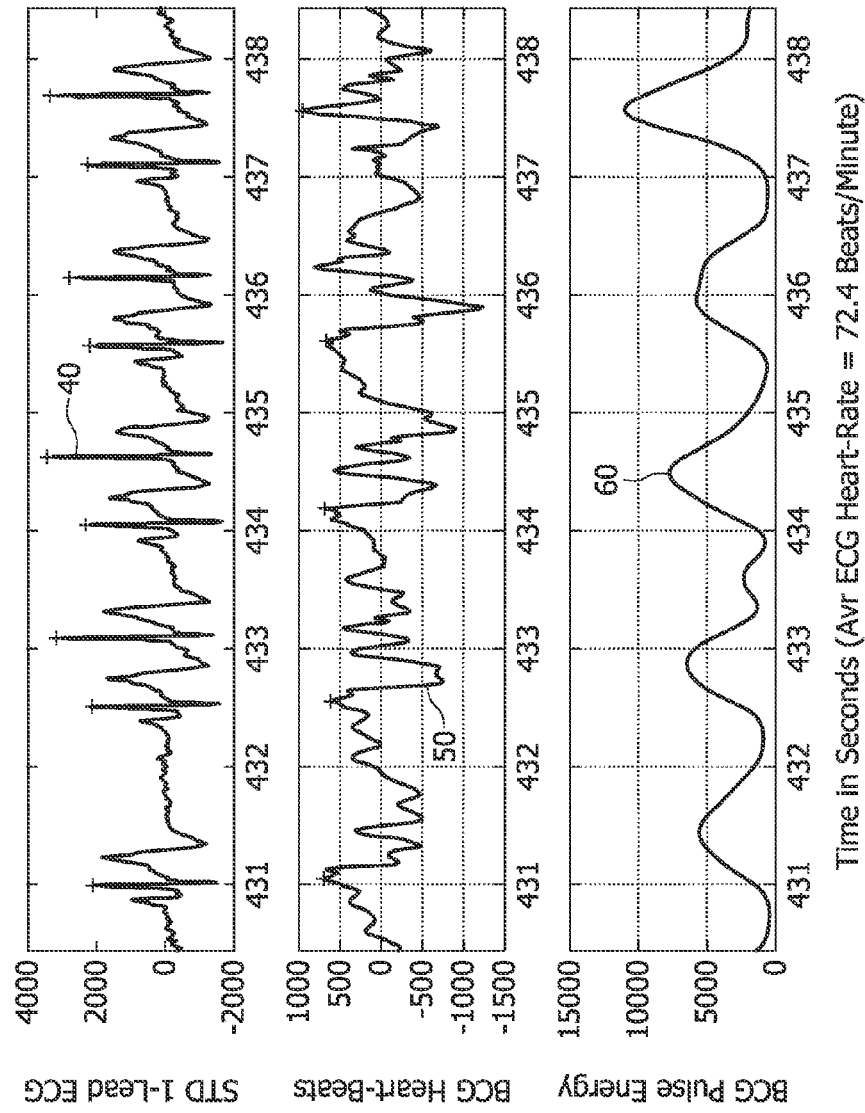
FIG. 4 depicts a ventricular arrhythmia captured by a one-lead ECG, the cardiac component of a BCG as well as the energy contained in the cardiac component of the BCG.

FIG. 4 depicts the same three panes as in FIG. 3 for a different subject over a time window of approximately 8 seconds. In this case, the top pane one-lead ECG reveals more R-peaks than there are ventricular contractions observed in the middle pane BCG; 9 R-Peaks from T=431s to T=438s in the ECG against 5 ventricular contractions in the BCG over the same period. This discrepancy is caused by the presence of a partial heart block in the subject's heart, which causes irregular conduction of the pulse generated by the SA-node through the conduction channels to the ventricles. For instance, the R-peak 40 fails to trigger a ventricular contraction as indicated by reference numeral 50. This causes a lack of energy content 60 in the integrated cardiac component of the BCG.

Hence, in this case, the evaluation of the cardiac component signal of the BCG reveals a distinct advantage over a standard one-lead ECG, since it allows to observe the true mechanical activity of the ventricles, instead of just monitoring the electrical activity of the heart. Consequently, the BCG may provide access to important information not present in a typical Holter recording. This is demonstrated in FIG. 4, where a (pathological) decoupling arises between the electrical and mechanical activity of the cardiac muscle, as shown in the differences between the ECG and the BCG traces.

In general, an ECG targets the detection of arrhythmias by employing a typical algorithm that identifies R-peaks in the ECG, which is the most prominent peak in the ECG. This is not possible in a BCG, since the BCG varies with body position and due to other circumstances, e.g. mechanical coupling of body to the sensor. For this reason, the BCG is typically evaluated using the earlier described methods e.g. by means of spectral analysis or auto-correlation.

Even though an occurring arrhythmia may be visible in the cardiac component of the BCG, it cannot be accurately detected in this component signal, for instance because the standard method of automated heart rate estimation used in an ECG cannot be applied to a BCG for the reasons given above. However, it has been demonstrated in FIG. 3 and FIG. 4 that an arrhythmia may be identified in the analysis of the energy of the cardiac component of the BCG due to the fact that the arrhythmic beat has a significantly lower mechanical impact, which most likely can be associated with a diminished ventricular activity in the case of such an arrhythmia.

Hence, when determining the actual energy content of the cardiac component of the BCG in the time window of interest and comparing this actual value with a reference energy content indicative of a regular heart rate over the same time window, the actual energy content of the cardiac component of the BCG in FIGS. 3 and 4 will deviate from the energy content of a regular heart rate during the same time window. Thus, by comparing the determined actual energy content and the reference energy content, the presence of the arrhythmia may be suspected when the difference between the actual energy content and the reference energy content exceeds a predefined threshold. The predefined threshold may be defined to incorporate tolerances for fluctuations in the signal to noise ratio of the cardiac component of the BCG.

The reference energy content $E_T$ of a time window may be determined in a number of ways. In an embodiment, the energy content $E_1$ of the part of a cardiac component of the BCG corresponding to a single heart beat is determined, e.g. by means of integration, and multiplied by the heart rate HR and the width T of the time window, such that:

$$E_T = E_1 * HR * T$$

This heart rate may be determined using known techniques for determining a heart rate in a BCG, as previously explained. This reference value may be recalculated after a number of time periods, e.g. after each evaluated time period in order to reduce the risk of inter-period fluctuations in the signal to noise ratio of the cardiac component of the BCG perturbing the arrhythmia determination. In case of a difference between the actual value and the reference value exceeding the predefined threshold, a further signal may be generated to indicate the presence of a possible arrhythmia in the time window under evaluation.

It will be appreciated that it may be difficult to determine an accurate heart rate from a single time window, especially when the time window exhibits one or more arrhythmias, since such arrhythmias will typically alter the effective heart rate in this time window. In an embodiment, an average heart rate is used in the above formula, which may be determined over a (large) number of time windows. This will provide a sufficiently accurate heart rate as long as the number of time windows including arrhythmias in said averaging is small compared to the total number of time windows used for said averaging.

Once the average heart rate has been determined, the energy content $E_1$ may be determined in a number of ways. For instance, the energy content of a known good time window, i.e. a time window comprising a number of heart beats corresponding to the average heart rate may be divided by the average heart rate to obtain $E_1$. However, in this case, the determination of $E_1$ may also be omitted and the actual energy content of the time window under evaluation may be directly compared to the actual energy content of the known good time window.

Alternatively, the detection of the ventricular contraction signal in the BCG may be used to define the boundary of a part of the time window under evaluation, with the other boundary being defined by the average heart rate. The energy content of the part of the BCG between the two boundaries defines $E_1$.

An alternative embodiment of the method of the present invention is based on the fact that for a regular heart beat, different time windows of the cardiac component have substantially identical energy contents. Hence, in this approach, the energy content of the cardiac component of the BCG in a first time window is compared to the energy content of the cardiac component of the BCG in a further time window having the same temporal width as the first window, and a further signal indicative of the possible presence of an arrhythmia is generated when the difference between the energy contents in the first and further windows exceeds a predefined threshold. The first window and the further window may be completely separated in time or may have some temporal overlap.

This facilitates a sliding window evaluation approach of the cardiac component of a BCG, in which the temporal window is continuously migrated over the cardiac component until a change in the energy content of the sliding window in excess of the predefined threshold is detected. This has the further advantage that the location of the potential arrhythmia can also be accurately determined because the most recently included heart beat in the sliding window will have caused the deviation in the energy content thereof.

This embodiment is particularly suitable for the monitoring of a subject suffering from regular arrhythmias for which the previous embodiment may be less suitable since it may be difficult to accurately determine an average heart rate. The main advantage of the sliding window approach is that no explicit knowledge of the actual heart rate is required to detect an arrhythmia in the BCG.

At this point, it is emphasized that even for a healthy patient, free of any cardiac arrhythmia's, there will be some variability of the successive heart-beat amplitudes which would have to be taken into account to ensure that the comparison between the overall BCG energy measure and the expected energy derived from the number of beats detected would be reliable.

For instance, it is well-known that the heart rate is sensitive to the respiration cycle. This known sinus respiratory manifestation leads to an acceleration of the heart rate during inhalation and vice-versa during exhalation. Hence, upon determination of the heart rate, this manifestation should be taken into account. It will be appreciated that the required respiratory data is readily available in the BCG; see e.g. FIG. 2b.

However, an embodiment of the present invention is based on the novel insight that the respiratory cycle has an additional impact of the energy content of a BCG. It has been found that the heart to sensor energy transfer is dependent on the phase of the respiration sinus; the body contact pressure on the ballistic sensor such as a sensor embedded in a mattress is increased when the thorax of the patient is moving up during inhalation, and is decreased during exhalation. These pressure variations affect the BCG successive heartbeat amplitude.

In the embodiment of the present invention, these variations are taken into account in the energy estimation step using a modulation function synchronized with the respiration sinus. The amplitude of the respiration process may be modeled as $f(t)=A(t)*\cos[2*\pi*\omega(t)]$ where $A(t)$ is the magnitude of the time-varying amplitude and $\omega(t)$ is the time-varying oscillation frequency. Both $A(t)$ and $\omega(t)$ can be estimated from the respiration signal extracted from the BCG signal by means of state-of-the-art techniques, for example, using the complex demodulation technique. From this parametric model of the respiration amplitude, a heuristic time-varying function is derived for compensating the modulations upon the BCG signal amplitude of the actual respiration process. This heuristic function has the same oscillatory period as the respiration process, i.e. the $\cos[2*\pi*\omega(t)]$ term, and differs through the "gain" factor tailored for reducing the BCG wave amplitude variations induced by the respiratory process.

It will be appreciated that such modulation is particularly suitable for application during sleep intervals of the subject under surveillance during which the breathing patterns of this subject are substantially constant, i.e. show little variations in the breathing period.

Since signal modulation is common general practice for the skilled practitioner, this will not be explained in further detail for reasons of brevity only. It will be appreciated that the modulation scheme will cause an increase of the cardiac component signal amplitude during an inhalation process and a decrease of the amplitude of this signal during an exhalation process to compensate for the aforementioned pressure variation effects.

Figure 5:
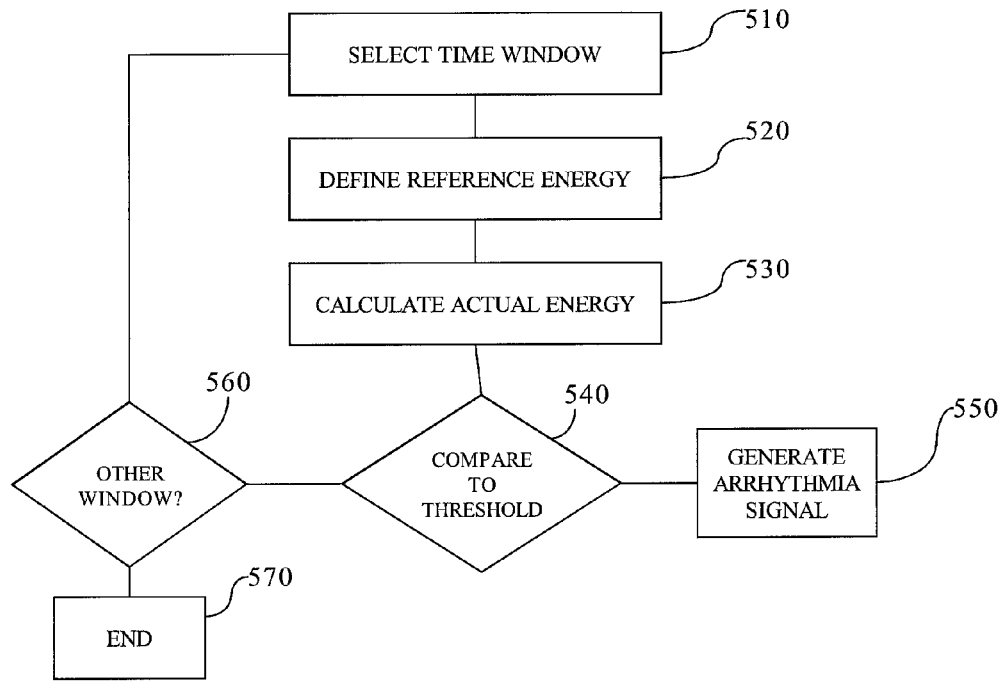
FIG. 5 depicts a flow chart of an embodiment of the method of the present invention.

An embodiment of the method of the present invention is summarized in the flow chart of FIG. 5.

In a first step 510, a time window of the recorded BCG is selected. This time window typically comprises a cardiac component signal incorporating a plurality of heart beats for the reasons mentioned before.

In a second step 520, a reference energy content for said time window is defined. This may be done using the aforementioned extrapolation approach based on the energy content of a single heart beat in the cardiac component signal of the BCG or by aforementioned sliding window approach in which the actual energy content of a time window is taken as the reference value.

In a next step 530, the calculating an actual energy content for said time window is calculated, e.g. by integration of the area under the cardiac component signal.

In step 540, comparing the actual energy content of the time window is compared with the reference energy content determined in step 520. At this point, it will be clear that in case of the sliding window approach, for the first window under evaluation, this will mean that the actual energy value is identical to the reference value. In this case, upon evaluation of a further window, an difference of the actual energy content of the further window compared to the energy content of the first window is indicative of the presence of a possible arrhythmia in either the first window or the further window. The determination of the energy content of further windows will clarify if the arrhythmia is present in the first window or the further window.

In case the comparison in step 540 detects a difference between the actual energy content and the reference energy content in excess of a predefined threshold, the method progresses to step 550 in which a further signal is generated indicative of the presence of a potential arrhythmia in the evaluated time window. This may trigger a medical practitioner to further evaluate the BCG and/or to perform further tests to diagnose the medical condition causing the arrhythmias.

The method may further comprise a check 560 to see if further time windows of the BCG are to be evaluated, e.g. in the case of a sliding window approach. If this is the case, the method may revert back to step 510. Otherwise, the method may terminate in step 570.

Figure 6:
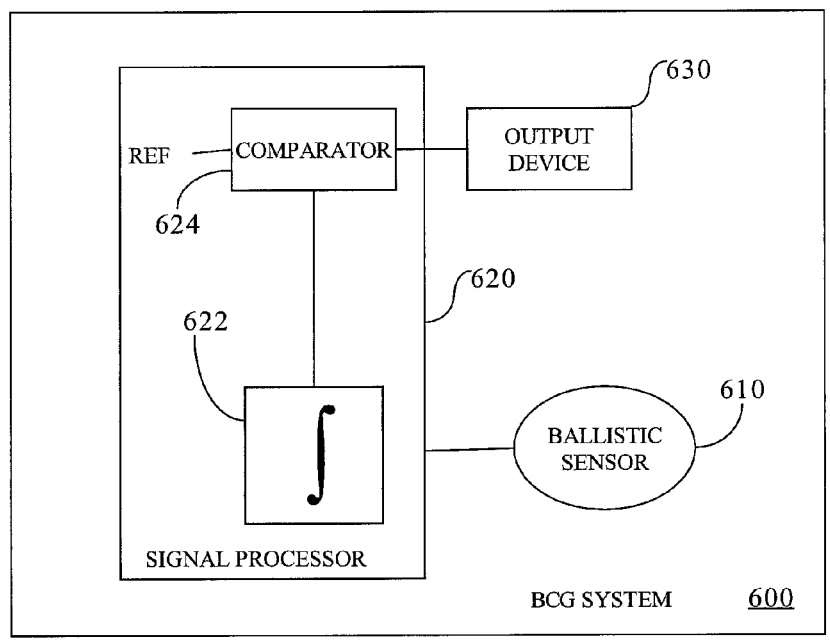
FIG. 6 schematically depicts a system in accordance with an embodiment of the present invention.

The method of the present invention may be implemented on a signal processing device 620 as shown in FIG. 6. In FIG. 6, the signal processing device 620 is integrated in a system 600 for recording a BCG. The system 600 typically comprises one or more ballistic sensors 610 coupled to the signal processing device 620, with the signal processing device 620 being arranged to evaluate the signals received from the one or more sensors 610. The sensors 610 may be any sensor suitable for recording a BCG.

It will be appreciated that although the signal processing device 620 is shown in conjunction with a system 600, the signal processing device 620 may also be supplied as a separate component, e.g. for use in existing BCG recording and/or evaluation systems.

The signal processing device 620 typically comprises an integrator 622 for integrating the cardiac component of the BCG signal received from the one or more sensors 610 to determine the actual energy content of this signal and a comparator 624 for comparing the actual energy content with a reference value REF to determine the presence of a possible arrhythmia in the selected time window. The comparator may be configured to generate a further signal indicative of the presence of the possible arrhythmia, which may be provided to an output device 630, e.g. a display, a loudspeaker and so on of the system 600.

The signal processing device 620 may further comprise further signal processing functionality (not shown) for isolating the cardiac and respiratory components of the BCG and for performing the necessary filtering and heart rate determination. The further signal processing functionality may further be arranged to define the boundaries of the time window, which may be in response to input from a user interface (not shown).

It should further be appreciated that although the integrator 622 and the comparator 624 are shown as separate components by way of non-limiting example only. It will be understood that it is equally feasible to implement at least some of this functionality in software on a processor. The integrator 622, the comparator 624 and the further signal processing functionality (not shown) may be integrated as separate hardware components on a single chip package, e.g. a system-on-chip architecture, a multi-chip module, a system-in-package and so on. Other alternative embodiments will be readily available to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of analyzing a ballistocardiogram to detect an arrhythmia comprising:
   selecting a first time window of interest of the ballistocardiogram, said first time window comprising a cardiac component signal incorporating a plurality of heart beats;
   defining a reference energy content including one of:
      determining a heart rate from said first time window and calculating the reference energy content by integrating an area under the cardiac component signal of a part of the cardiac component signal incorporating a single heart beat and multiplying the calculated energy content by the determined heart rate and first time window duration,
      OR
      defining a further time window of the ballistocardiogram by displacing the first time window by a predefined amount of time and determining the reference energy content by integrating an area under the cardiac component signal over the further time window;
   calculating an actual energy content including one of:
      determining a heart rate from said first time window and calculating the actual energy content by integrating an area under the cardiac component signal of a part of the cardiac component signal incorporating a single heart beat and multiplying the calculated energy content by the determined heart rate and first time window duration,
      OR
      defining a further time window of the ballistocardiogram by displacing the first time window by a predefined amount of time and determining the actual energy content by integrating an area under the cardiac component signal over the further time window,
   comparing the calculated actual energy content with the determined reference energy content; and
   generating an arrhythmia signal when a difference between the actual energy content and the reference energy content exceeds a predefined threshold.

2. The method according to claim 1, further comprising:
generating the cardiac component signal by separating the cardiac component signal from a respiratory component signal of the ballistocardiogram.

3. The method according to claim 1, further comprising:
determining a respiration pattern during said time window; and
modulating the cardiac component signal in accordance with the determined respiration pattern.

4. The method according to claim 3, wherein said modulating comprises increasing the amplitude of the signal during an inhalation process and reducing the amplitude of the signal during an exhalation process.

5. A signal processing device configured to:
select a time window of interest of a ballistocardiogram, said time window of interest comprising a cardiac component signal incorporating a plurality of heart beats;
determine a heart rate from said time window of interest;
define a reference energy content by integrating an area under a part of the cardiac component signal incorporating a single regular heart beat and multiplying the calculated energy content by the determined heart rate and a duration of the time window;
determine an actual energy content by integrating an area under the cardiac component signal over the time window of interest;
compare the actual energy content with the reference energy content;
generate an output signal when a difference between the actual energy content and the reference energy content exceeds a predefined threshold; and
wherein the output signal is indicative of an arrhythmia and further including an output device which receives the output signal and outputs an indication of the occurrence of the arrhythmia.

6. The signal processing device according to claim 5, further being configured to define a further time window of the ballistocardiogram by displacing the time window by a predefined amount of time.

7. The signal processing device according to claim 5, further being configured to:
determine a respiration pattern during said time window; and
modulate the cardiac component signal in accordance with the determined respiration pattern.

8. A system comprising:
at least one ballistic sensor for recording the ballistocardiogram; and
the signal processing device according to claim 5, wherein the at least one ballistic sensor is coupled to the signal processing device.

9. The system according to claim 8, wherein the ballistocardiogram sensor is integrated in a structure configured for supporting body weight.

10. A signal processing device configured to:
receive a ballistocardiogram;
select a first time window of the ballistocardiogram, said first time window including a cardiac component signal spanning a plurality of heart beats;
integrating an area under the cardiac component signal in said first time window; define a further time window of the ballistocardiogram by displacing the first time window by a predefined amount of time;
integrating an area under the cardiac component signal over the further time window;
compare the integrated area over the further time window with the integrated area over the first time window;
generate an output signal when a difference between the integrated areas over the further time window and the first time window exceeds a predefined threshold; and
wherein the output signal is indicative of an arrhythmia and further including an output device which receives the output signal and outputs an indication of the occurrence of the arrhythmia.

11. The signal processing device according to claim 10, further being configured to:
generate the cardiac component signal by separating the cardiac component signal from a respiratory component signal of the ballistocardiogram.

12. A system comprising:
the signal processing device according to claim 10; and
a ballistic sensor configured to sense the ballistocardiogram.

* * * * *